United States Patent [19]
Dessau et al.

[11] Patent Number: 6,005,123
[45] Date of Patent: Dec. 21, 1999

[54] EPOXIDATION PROCESS

[75] Inventors: Ralph M. Dessau, Edison, N.J.; Andrew P. Kahn, Eagleville; Roger A. Grey, West Chester, both of Pa.

[73] Assignee: Arco Chemical Technology, L.P., Greenville, Del.

[21] Appl. No.: 09/290,100

[22] Filed: Apr. 12, 1999

Related U.S. Application Data

[60] Provisional application No. 60/081,939, Apr. 16, 1998.

[51] Int. Cl.$^6$ ....................... C07D 301/12; C07D 303/04
[52] U.S. Cl. ............................................... 549/531
[58] Field of Search ................................. 549/531

[56] References Cited

U.S. PATENT DOCUMENTS 4,410,501  10/1983  Taramasso et al. .................. 423/326
5,599,956  2/1997  Pujado et al. ........................ 549/531

FOREIGN PATENT DOCUMENTS

| 19600709 | 7/1997 | Germany . |
| 4-352771 | 12/1992 | Japan . |
| 8-269029 | 10/1996 | Japan . |
| 8269030 | 10/1996 | Japan . |

*Primary Examiner*—Ba K. Trinh
*Attorney, Agent, or Firm*—William C. Long

[57] ABSTRACT

The selectivity of an olefin epoxidation catalyzed by a noble metal-modified titanium or vanadium zeolite is greatly enhanced by the addition of a phosphorus, sulfur, selenium or arsenic compound to the reaction mixture. The epoxidation utilizes hydrogen and oxygen in addition to the olefin.

19 Claims, No Drawings

EPOXIDATION PROCESS

RELATED APPLICATION

This application claims the benefit of Provisional Application 60/081,939 filed Apr. 16, 1998.

FIELD OF THE INVENTION

This invention relates to methods of oxidizing olefins to obtain epoxides. More particularly, this invention pertains to an improved epoxidation process wherein a phosphorus, sulfur, selenium or arsenic-containing modifier such as triphenyl phosphine is utilized to enhance the selectivity of a titanium or vanadium zeolite catalyst which has been modified with a noble metal such as palladium.

BACKGROUND OF THE INVENTION

Epoxides constitute an important class of chemical intermediates useful for the preparation of polyether polyols, glycols, glycol ethers, surfactants, functional fluids, fuel additives and the like. Many different methods for synthesizing epoxides from the corresponding olefins have been described in the literature. A Japanese patent application assigned to the Tosoh Corporation and published in 1992 (Kokai No. 4-352771) proposed making propylene oxide by reacting propylene, hydrogen and oxygen using a catalyst comprising a Group VIII metal and a crystalline titanosilicate. Improvements to or variations of this basic process were subsequently described in the following published patent applications: WO 97/25143, DE 19600709, WO 96/02323, WO 97/47386, WO 97/31711, JP H8-269030, and JP H8-269029.

As with any chemical process, it would be desirable to attain still further improvements in epoxidation methods of this type. In particular, increasing the selectivity to epoxide and extending the useful life of the catalyst would significantly enhance the commercial potential of such methods. Using the reaction conditions and catalysts described in the literature, for example, hydrogenation of the olefin to the corresponding saturated hydrocarbon competes with the desired epoxidation reaction. The discovery of more effective ways of suppressing this side-reaction would be highly advantageous.

SUMMARY OF THE INVENTION

This invention provides a process for producing an epoxide comprising reacting an olefin, hydrogen and oxygen in the presence of (a) a catalyst comprised of a titanium or vanadium zeolite and a noble metal and (b) a phosphorus, sulfur, selenium or arsenic compound modifier at a temperature effective to form the epoxide corresponding to the olefin.

DETAILED DESCRIPTION OF THE INVENTION

The catalysts to be used in the present process are comprised of a titanium or vanadium zeolite and a noble metal (preferably an element of Group VIII of the Periodic Table). Suitable zeolites are those crystalline materials having a porous molecular sieve structure with titanium or vanadium atoms substituted in the framework. The choice of zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite or vanadium silicalite is especially advantageous. For a bulky olefin such as cyclohexene, a larger pore titanium zeolite such as a titanium zeolite having a structure isomorphous with zeolite beta may be preferred.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are well known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta, mordenite, ZSM-48, ZSM-12, and MCM-41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2$ $(1-x)SiO_2$ where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent. The manner in which the noble metal is incorporated into the catalyst is not considered to be particularly critical. For example, the noble metal may be supported on the zeolite by impregnation means or the like or first supported on another substance such as silica, alumina, activated carbon or the like and then physically mixed with the zeolite. Alternatively, the noble metal can be incorporated into the zeolite by ion-exchange with, for example, Pd tetraammine chloride with or without added ammonium hydroxide. The catalyst is recovered by filtration and washing and is substantially free (<0.1 wt. %) of halide. There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals. Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound after being introduced into the catalyst may be fully or partially pre-reduced. Satisfactory catalytic performance can, however, be attained without any pre-reduction whatsoever. To achieve the active state of palladium, the catalyst may undergo pretreatment such as thermal treatment in nitrogen, vacuum, hydrogen or air.

The catalyst may additionally comprise a binder or the like and may be molded, spray dried, shaped or extruded into any desired form prior to use in epoxidation. In addition to the noble metal, the catalyst may be modified with additional elements such as, for example, lanthanide metals (e.g., europium), iron, cobalt, nickel, boron, aluminum, phosphorus, calcium, vanadium, chromium, manganese, copper, zinc, gallium or zirconium.

Suitable catalysts for use in the process of this invention as well as methods for their preparation are described in more detail in the following published patent applications, each of which is incorporated herein by reference in its entirety: U.S. Pat. No. 5,859,265, JP 4-352771, WO 97/31711, DE 19600709, WO 96/02323, WO 97/47386, WO 97/25143, JP H8-269030 and JP H8-269029.

The aforedescribed catalyst is used in accordance with the invention in combination with a phosphorus, sulfur, selenium or arsenic compound modifier. Although the precise mechanism by which the modifier operates is not known, these compounds when present during epoxidation usually have the beneficial effect of suppressing the undesirable hydrogenation of the olefin to its saturated hydrocarbon counterpart and thereby greatly improving the selectivity to the desired epoxide. In certain cases it is desirable to employ a modifier having a molecular cross-section greater than the pore diameter of the titanium zeolite. For example, when TS-1 titanium silicalite is the titanium zeolite, the modifier preferably has a molecular cross-section greater than about 6 angstroms. General classes of phosphorus modifiers suitable for use include organic phosphines, organic phosphine oxides, organic phosphites, and organic phosphates. Analogous organic arsines and organic arsine oxides can be used. Organic phosphines and organic phosphine oxides are particularly preferred for use in modifiers, especially phosphines and phosphine oxides bearing three organic substituents (i.e., tertiary organophosphines). Preferably at least one, and most preferably all three substituents are aryl groups such as phenyl and substituted phenyl. Triphenylphosphine, triphenyl phosphine oxide, and methyldiphenylphosphineoxide are examples of particularly effective modifiers. Examples of organic phosphates are trialkyl phosphates such as triethyl or trimethyl phosphate and examples of organic phosphites are phosphorous acid trialkyl esters such as phosphorous acid triethyl ester, phosphorous acid trimethyl ester, and the like. Organic diphosphines and organic diphosphine oxides can be used such as 1,2-bis (diphenylphosphino) ethane, 1,3-bis (diphenylphosphino) propane, 1,4-bis (diphenylphosphino) butane, 1,1-bis (diphenylphosphino) ferrocene and O-isopropylidene-2,3-dihydroxy-1,4-bis (diphenylphosphino) butane. Comparable arsenic compounds such as triphenyl arsine, triphenyl arsine oxide, and the like are useful. Organic sulfur compounds are useful such as benzothiophene and dibenzothiophene. Analogous selenium compounds can be used. While the catalyst could be treated with the modifier either prior to or after introduction of the noble metal and either prior to or after reduction of the noble metal prior to use of the catalyst in epoxidation, in one particularly preferred and convenient embodiment of the invention the modifier is simply added to the reaction medium in which the epoxidation is being performed. The modifier may be introduced to the reaction medium all at once either prior to or following initiation of epoxidation or may be added in an incremental or continuous manner.

The amount of modifier used is not believed to be particularly critical, but at a minimum should be effective to improve selectivity to the epoxide as compared to the same reaction carried out under similar conditions in the absence of the modifier. While the use of large amounts of modifier is not believed to interfere with epoxidation, beyond a certain level little further improvement in catalytic performance may be realized. Generally speaking, however, modifier:noble metal molar ratios in the range of from about 100:1 to 0.01:1 (more preferably, from about 50:1 to 0.05:1) are typically suitable.

The olefin to be used can be any organic compound containing at least one site of ethylenic unsaturation (i.e., at least one carbon-carbon double bond). The olefin can be aliphatic, aromatic or cycloaliphatic in character and may have either a linear or branched structure, with the site(s) of ethylenic unsaturation being terminal and/or internal. The olefin preferably contains 2–30 carbon atoms; the process of the invention is particularly suitable for epoxidizing $C_2$–$C_6$ mono-olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro, groups or the like.

Typical examples of suitable olefins include ethylene, propylene, 1-butene, cis- and trans-2-butene, isobutene, 1,3-butadiene, pentenes, isoprene, hexenes, octenes, nonenes, decenes, undecenes, dodecenes, cyclopentene, cyclohexene, dicyclopentadiene, vinylcylohexane, vinyl cyclohexene, allyl chloride, allyl alcohol, methallyl chloride, methallyl alcohol, alkyl acrylates and methacrylates, unsaturated fatty acids and esters thereof, styrene, -methylstyrene, divinylbenzene, indene and stilbene. Mixtures of olefins may, of course, be utilized if so desired. The process of this invention is especially useful for converting propylene to propylene oxide.

The process of the invention may be suitably conducted under the reaction conditions (e.g., temperature, pressure, reactant ratios) described in the following published patent applications, provided the necessary modifier previously described herein is present while the olefin, hydrogen and oxygen are being contacted with the catalyst: WO 96/02323, WO 97/25143, DE 19600709, WO 97/31711, WO 97/47386, JP 4-352771, JP H8-269029, and H8-269030.

The amount of catalyst used may be determined on the basis of the molar ratio of the titanium contained in the titanium zeolite to the olefin that is supplied per unit of time. Typically, sufficient catalyst is present to provide a titanium/olefin fed ratio of from 0.00001 to 0.1. The time required for the epoxidation may be determined on the basis of the gas hourly space velocity, i.e., the total volume of olefin, hydrogen, oxygen and carrier gas(es) per hour per unit of catalyst volume (abbreviated as GHSV). A GHSV in the range of 10 to 10,000 $hr^{-1}$ is typically satisfactory.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid phase, it is advantageous to work at a pressure of 1–100 bars and in the presence of one or more solvents. Suitable solvents include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water.

Epoxidation according to the invention is carried out at a temperature effective to achieve the desired olefin epoxidation, preferably at temperatures in the range of 0–125° C. (more preferably, 20–80° C.). The molar ratio of hydrogen to oxygen can usually be varied in the range of $H_2:O_2=1:10$ to 5:1 and is especially favorable at 1:5 to 2:1. The molar ratio of oxygen to olefin is usually 1:1 to 1:20, and preferably 1:1.5 to 1:10. Relatively high $O_2$ to olefin molar ratios (e.g., 1:1 to 1:3) may be advantageous for certain olefins. As the carrier gas, any desired inert gas can be used. The molar ratio of olefin to carrier gas is then usually in the range of 1:100 to 4:1, and especially 20:1 to 1:1.

As the inert carrier gas, noble gases such as helium, neon, argon, krypton, and xenon are suitable in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

EXAMPLES

A catalyst containing 0.5 weight percent Pd was prepared by impregnating a solution of $PdBr_2$ in ammonium hydroxide onto a TS-1 titanium silicalite containing 1.1 weight percent Ti. The catalyst was dried and used as is without prior reduction with hydrogen. The epoxidation reaction was conducted at atmospheric pressure using 3 g catalyst at 45° C. in 100 mL methanol. The gaseous feed to the reactor consisted of 44 cc/min of 5% $O_2$ in $N_2$ and 6 cc/min of an 80/20 mixture of propylene/$H_2$. A methanol-containing vaporizer was placed in the feed line to prevent evaporative loss of the reactor solvent. Reactor effluents were analyzed directly by on-line gas chromatography.

After 218.5 hours on stream, a solution of 0.2 g triphenyl phosphine in 20 mL methanol was added to the reaction mixture. The amount of propylene oxide in the reactor effluent dropped upon triphenyl phosphine addition, but later increased to a higher level than before triphenyl phosphine addition (>1600 ppm v. ca. 1200 ppm). Most importantly, the amount of propane in the reactor effluent (from hydrogenation of propylene) decreased significantly upon triphenyl phosphine addition and remained low. Selectivity to propylene oxide (propylene oxide/propylene oxide+ propane) was greater than 95% after introduction of the triphenyl phosphine as compared to less than 60% prior to triphenyl phosphine addition. Oxygen utilization for propylene oxide formation ($PO/O_2$ Consumed) was also higher after phosphine addition (40%) than before phosphine addition (ca. 33%).

The epoxidation was repeated, but using 120 mL methanol and 0.22 g triphenyl phosphine oxide as the modifier added from the start of the run. A selectivity to propylene oxide of 98% or greater was observed during the first 95 hours on stream at which time reactor effluent propylene oxide yield stood at 1100 ppm. The selectivity thereafter decreased gradually to 90% at 165 hours on stream as the propylene oxide yield rose to 1600 ppm.

A series of additional experimental runs was made. The reaction was carried out at 45° C. and 3 psig in a glass reactor with a teflon stirring bar (1000 rpm) except for Run 6 which was carried out at 60° C. Gas flow rate into the reactor was 25.1 cc/min. propylene/hydrogen (20 vol % hydrogen) and 88.0 cc/min. nitrogen/oxygen/methane (by volume 5% $O_2$, 0.6% methane, balance nitrogen). A solvent containing vaporizer was placed in the feed line to prevent evaporative loss of the reactor solvent. In Runs 1–6, 3 grams of catalyst in 112 grams of methanol/water (75/25 by wt) were used, in Run 7, 3 grams of catalyst in 130 grams of water was used. Reactor effluents were analyzed directly by on-line gas chromatography.

In the Runs, the reaction was carried out until steady state conditions were achieved at which point the designated phosphine in about 10 cc of the reaction solvent was added. In Runs 1–5, 200 mg. of phosphine was added, in Runs 6–7 190 mg of phosphine oxide was added.

The following Table shows the steady state concentrations of propane and propylene oxide in the reactor effluent before and after the phosphine addition.

TABLE 1

| RUN NUMBER | CATALYST | PHOSPHINE[1] | VOLUME % PO/PROPANE BEFORE PHOSPHINE | VOLUME % PO/PROPANE AFTER PHOSPHINE |
|---|---|---|---|---|
| 1 | A | TPP | 0.35/0.42 | 0.34/0.08 |
| 2 | A | TPP | 0.35/0.16 | 0.25/0.06 |
| 3 | A | TPP | 0.34/0.26 | 0.28/0.05 |
| 4 | B | TPP | 0.18/0.2 | 0.31/0.05 |
| 5 | C | TPP | 0.3/0.16 | 0.4/0.01 |
| 6 | D | DPPO | 0.2/0.4 | 0.28/0.18 |
| 7 | E | DPPO | 0.12/0.08 | 0.07/0.01 |

[1]TPP = triphenyl phosphine
DPPO diphenylmethyl phosphine oxide
The catalysts used above were prepared as follows:

Catalyst A

Palladium tetraammine nitrate (7.77 grams) was dissolved in 310 grams of 25 wt % aqueous ammonium hydroxide, stirred at 23° C. for 3 days and filtered. In a single-neck round-bottom flask 15 grams of TS-1 titanium silicalite (2.1 wt % titanium, calcined at 550° C. in air for 4 hrs) was slurried in 60 grams of deionized water. To this slurry, 7.1 grams of the palladium tetraammine nitrate solution was added and heated at 80° C. under a nitrogen atmosphere for 24 hrs. The liquid was removed by rotoevaporation at 50° C. The solids were dried in a vacuum oven at 60° C. for 24 hrs. These solids were then calcined in an oven under a nitrogen atmosphere at 150° C. for 4 hrs. The catalyst contained about 0.5 wt % Pd.

Catalyst B

An Erlenmeyer flask equipped with a teflon coated stir bar was charged with 30 grams of TS-1 titanium silicalite (1.2 wt % titanium, calcined in air at 550° C.) and 100 grams of deionized water. Palladium tetraammine dichloride hydrate (0.38 grams) was dissolved in 15 grams of 30 wt % ammonium hydroxide and added to the titanium silicalite slurry over a 10 minute period. The reaction mixture was allowed to stir at 23° C. for 24 hrs. The slurry was centrifuged and the liquid decanted. The solids were washed with deionized water four times. The solids were dried in a vacuum oven at 50° C. for 4 hrs. The dried solids were then transferred to a glass tube and treated with nitrogen (100 cc/min) at 150° C. for 4 hrs. The catalyst contained about 0.5 wt % Pd.

Catalyst C

This catalyst was prepared in a manner similar to that for Catalyst A except that twice as much palladium tetraammine nitrate was used to give a catalyst which contained about 1% Pd.

Catalyst D

An erlenmeyer flask equipped with a teflon coated stir bar was charged with 30 grams of TS-1 titanium silicalite (2.1 wt % titanium, calcined in air at 550° C.) and 100 grams of deionized water. Palladium dibromide (0.38 grams) was dissolved in 15 grams of 30 wt % ammonium hydroxide and added to the titanium silicalite slurry over a 10 minute period. The reaction mixture was allowed to stir at 23° C. for 2 hrs. The liquid was removed by rotoevaporation at 50° C. The solids were dried in a vacuum oven at 50° C. for 4 hrs. The dried solids were then transferred to a glass tube and treated with nitrogen (100 cc/min) at 150° C. for 4 hrs. The catalyst contained about 0.5 wt % Pd.

Catalyst E

An Erlenmeyer flask equipped with a teflon coated stir bar was charged with 30 grams of TS-1 titanium silicalite (1.2 wt % titanium, calcined in air at 550° C.) and 100 grams of deionized water. Palladium dibromide (0.095 grams) was dissolved in 15 grams of 30 wt % ammonium hydroxide and added to the titanium silicalite slurry over a 10 minute period. The reaction mixture was allowed to stir at 23° C. for 2 hrs. The liquid was removed by rotoevaporation at 50° C. The solids were dried in a vacuum oven at 50° C. for 4 hrs. The dried solids were then transferred to a glass tube and treated with nitrogen (100 cc/min) at 150° C. for 4 hrs. The catalyst contained about 0.125 wt % Pd.

As can be seen from the results reported in Table 1, the phosphine addition in each case sharply reduced propane production thus greatly enhancing selectivity of the propylene conversion to the desired propylene oxide product.

Using Catalyst D is above described, Run 8 was carried under same reaction conditions but with the addition of 100 mg. of benzothiophene in 10 grams of methanol. The results are given in the following Table 2 and clearly demonstrate the sharply reduced propane made as a result of the modifier addition.

TABLE 2

| RUN NUMBER | CATA-LYST | ADDITIVE | VOL % PO/PROPANE BEFORE SULFIDE | VOL % PO/PROPANE AFTER SULFIDE |
|---|---|---|---|---|
| 8 | D | BENZO-THIOPHENE | 0.22/0.42 | 0.12/0.01 |

We claim:

1. A process for producing an epoxide comprising reacting an olefin, hydrogen and oxygen in the presence of (a) a catalyst comprised of a titanium or vanadium zeolite and a noble metal and (b) a phosphorus, sulfur, selenium or arsenic compound modifier at a temperature effective to form the epoxide corresponding to the olefin.

2. The process of claim 1 wherein the modifier is selected from the group consisting of organic phosphines, organic phosphine oxides, organic phosphites, and organic phosphates.

3. The process of claim 1 wherein the modifier is selected from the group consisting of organic phosphines and organic phosphine oxides.

4. The process of claim 1 wherein the modifier has a molecular cross-section greater than the pore diameter of the titanium zeolite.

5. The process of claim 1 wherein the titanium zeolite is titanium silicalite.

6. The process of claim 1 wherein the olefin is a $C_2$–$C_6$ mono-olefin.

7. The process of claim 1 wherein the noble metal is palladium.

8. A process for producing an epoxide comprising reacting a $C_2$–$C_6$ mono-olefin, hydrogen and oxygen in the presence of (a) a catalyst comprised of titanium or vanadium silicalite and palladium and (b) a modifier selected from the group consisting of organic phosphines, organic phosphine oxides, organic phosphites, and organic phosphates at a temperature of from 20° C. to 80° C. to form the epoxide corresponding to the $C_2$–$C_6$ mono-olefin.

9. The process of claim 8 wherein the modifier is a phosphine or phosphine oxide having three organic substituents.

10. The process of claim 8 wherein the organic substituents are aryl substituents.

11. The process of claim 8 wherein the modifier is selected from the group consisting of triphenyl phosphine, triphenyl phosphine oxide, and mixtures thereof.

12. The process of claim 8 wherein the $C_2$–$C_6$ mono-olefin is propylene.

13. The process of claim 8 wherein the titanium silicalite is TS-1.

14. The process of claim 8 wherein said reaction is carried out in a liquid medium.

15. The process of claim 13 wherein the liquid medium is comprised of methanol and water.

16. The process of claim 13 wherein the modifier is introduced into said liquid medium.

17. The process of claim 7 wherein the catalyst is comprised of from 0.1 to 5.0 weight percent Pd.

18. The process of claim 7 wherein the molar ratio of modifier:noble metal is in the range of from 50:1 to 0.05:1.

19. The process of claim 1 wherein the modifier is an organic sulfur compound.

* * * * *